United States Patent
Kool et al.

(10) Patent No.: US 10,405,957 B2
(45) Date of Patent: Sep. 10, 2019

(54) METHOD AND SYSTEM FOR GENERATING AN OESTRUS ATTENTION SIGNAL FOR A CATTLE ANIMAL

(71) Applicant: LELY PATENT N.V., Maassluis (NL)

(72) Inventors: Pieter Neelus Kool, Hardinxveld-Giessendam (NL); Adolf Jan Van Der Kamp, Zwolle (NL); Patrick Philip Jacob Van Der Tol, Barendrecht (NL)

(73) Assignee: Lely Patent N.V., Maassluis (NL)

( * ) Notice: Subject to any disclaimer, the term of this patent is extended or adjusted under 35 U.S.C. 154(b) by 0 days.

(21) Appl. No.: 14/760,102

(22) PCT Filed: Dec. 12, 2013

(86) PCT No.: PCT/NL2013/050893
§ 371 (c)(1),
(2) Date: Jul. 9, 2015

(87) PCT Pub. No.: WO2014/109633
PCT Pub. Date: Jul. 17, 2014

(65) Prior Publication Data
US 2015/0351885 A1    Dec. 10, 2015

(30) Foreign Application Priority Data
Jan. 9, 2013  (NL) ..................... 2010098

(51) Int. Cl.
*A61D 17/00* (2006.01)
*A01K 29/00* (2006.01)
(Continued)

(52) U.S. Cl.
CPC .......... *A61D 17/002* (2013.01); *A01K 29/005* (2013.01); *A61B 5/1118* (2013.01); *A61B 5/7282* (2013.01); *A61B 2503/40* (2013.01)

(58) Field of Classification Search
CPC .......................... A61K 29/005; A61D 17/002
(Continued)

(56) References Cited

U.S. PATENT DOCUMENTS

| | | | | |
|---|---|---|---|---|
| 2009/0187392 A1* | 7/2009 | Riskey | ................. | A01K 29/005 703/11 |
| 2010/0324861 A1* | 12/2010 | Goulding | ............. | A01K 29/005 702/150 |

(Continued)

FOREIGN PATENT DOCUMENTS

| FR | 2 759 541 A1 | 8/1998 |
|---|---|---|
| WO | WO 2011/013538 A1 | 2/2011 |

(Continued)

OTHER PUBLICATIONS

"circuitry" The American Heritage Dictionary of the English Language, Fifth Edition (2014), Houghton Mifflin Harcourt Publishing Company. Retrieved from <https://ahdictionary.com/word/search.html?q=circuitry> on Jun. 13, 2015.*

(Continued)

*Primary Examiner* — David J. McCrosky
(74) *Attorney, Agent, or Firm* — Oblon, McClelland, Maier & Neustadt, L.L.P.

(57) ABSTRACT

A method for monitoring oestrus of a cattle animal, for example a cow. The method includes: a) collecting activity data of the animal, b) computing a current activity level based on the activity data, c) deciding whether to generate an oestrus attention signal by comparing at least one current activity level to a corresponding baseline activity level. The computing b) further includes b1) detecting travelling movements of the animal and b2) correcting the baseline activity level for detected travelling movements.

6 Claims, 2 Drawing Sheets

Figure 1:
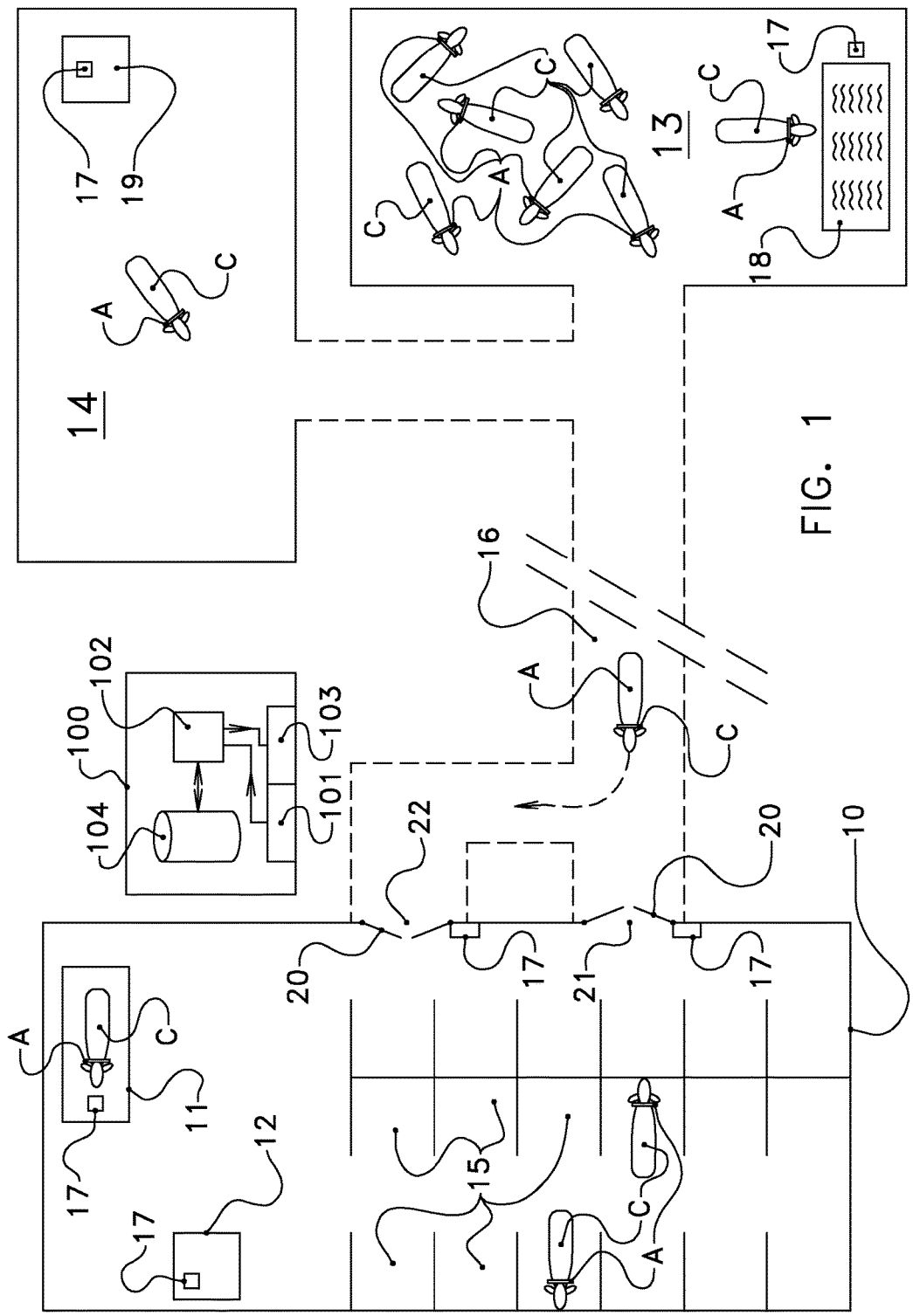

(51) Int. Cl.
    *A61B 5/11*         (2006.01)
    *A61B 5/00*         (2006.01)

(58) Field of Classification Search
    USPC .......................... 600/551; 340/573.1, 573.3
    See application file for complete search history.

(56) References Cited

U.S. PATENT DOCUMENTS

| | | |
|---|---|---|
| 2012/0238912 A1 | 9/2012 | Rajkondawar et al. |
| 2012/0274442 A1* | 11/2012 | Mottram ............. A01K 29/005 340/5.8 |
| 2013/0269618 A1 | 10/2013 | Song et al. |

FOREIGN PATENT DOCUMENTS

| | | | |
|---|---|---|---|
| WO | WO 2012/078033 A1 | 6/2012 | |
| WO | WO 2012078033 A8 * | 2/2013 | ........... A01K 29/005 |

OTHER PUBLICATIONS

"circuit" Oxford English Dictionary, Oxford University Press (2015). Retrieved from <http://www.oxforddictionaries.com/us/definition/american_english/circuit> on Jun. 13, 2015.*

Firk, et al. "Automation of oestrus detection in dairy cows: a review." Livestock Production Science 75.3 (2002): 219-232.*

Wagnon, et al. "Estrous behavior and stress effects on the estrous cycle of range beef heifers" (1972) California Agricultural Experiment Station. Berkeley, Cal . vol. B0858. p. 3-16. Retrived from <http://ucce.ucdavis.edu/files/repository/100758.pdf> on May 2, 2017.*

International Search Report dated Mar. 11, 2014 in PCT/NL2013/050893.

* cited by examiner

METHOD AND SYSTEM FOR GENERATING AN OESTRUS ATTENTION SIGNAL FOR A CATTLE ANIMAL

TECHNICAL FIELD

The invention relates to method for monitoring oestrus of a dairy cattle animal. The invention further relates to a system for generating an oestrus attention signal for a cattle animal, a computer program product, a computer readable medium and a computer device.

PRIOR ART

Reliable oestrus detection of cattle animals is important for farm holders to meet their reproduction goals. The number of false positives and false negatives should be as low as possible.

Different oestrus detection methods are known. As dairy cattle show increased activity in association with oestrus, these methods include activity based methods which measure an activity level of an animal and generate an oestrus attention signal if the activity level is high than normal.

In *Automation of oestrus detection in dairy cows: a review*, by Firk et al (Livestock Production Science 75 (2002) 219-232) the use of a pedometer in this context is described.

In *Analysis of Activity Measurement for Accurate Oestrus Detection in Dairy Cattle*, by Koelsch et al (J. agric. Engng Res. (1994) 58, 107-114) activity based oestrus detection is described. It is described that dioestrus animals follow similar, constant patterns of daily activity that include two periods of high activity: feeding and milking. It is suggested that a comparison of activity data for the test day and base line period must be matched for the same time of day to take this into account.

However, such a method has the disadvantage that animals do exhibit varying activity patterns, especially in situations wherein milking is done by milking robots and feeding robots which the animal can visit when it wants. Also in free grazing systems, animals may exhibit varying activity patterns, caused by unexpected events like passing trains, aircrafts and (possibly landing) hot air balloons.

BRIEF DESCRIPTION

It is an object to provide a more reliable method for generating an oestrus attention signal for a dairy cattle animal.

According to an aspect there is provided a method for monitoring oestrus of a cattle animal, in particular a cow, the method comprising:
a) collecting activity data of the animal,
b) computing a current activity level based on the activity data,
c) deciding whether to generate an oestrus attention signal by comparing at least one current activity level to a corresponding baseline activity level,
characterized in that action b) further comprises
b1) detecting travelling movements of the animal and
b2) correcting the current activity level for detected travelling movements.

The baseline activity level and the current activity level are both indications of the activity, the baseline activity level being an indication of the activity in a first time interval and the current activity level being an indication of the activity in a second time interval, the second time interval being shorter than the first time interval and the second time interval being more recent than the first time interval. Thus, the current activity level, i.e. the activity as determined for the shorter and more recent time interval, can be compared with the baseline activity level, e.g. to see if certain deviations give rise to specific measures or the like.

Herein, activity data relate to movements of the animal that may be an indication of oestrus, that is movements that are ordinarily considered when monitoring an animal for oestrus. Such movements may comprise leg movements, in particular steps, and/or head/neck movements, such as shaking the head from left to right or up and down, and/or displacements of the animal, i.e. walking, or the like.

The collecting of activity data under a) may be performed by any suitable activity measuring device, such as in particular a motion detector (including an accelerometer), for instance embodied by a pedometer attached to a leg of the animal, a motion detector attached to a collar of the animal, an animal locator, video observation systems, animal identification devices positioned at different locations, etc. Often, activity data are collected as sets of numbers of movements during certain consecutive time intervals, such as the number of steps during one-hour intervals. Then, e.g. the current activity level relates to the detected movements (such as the number thereof) in the current (i.e. last) interval or intervals, while the baseline activity level relates e.g. similarly to the detected movements (such as the number thereof) during at least one interval preceding the last interval, possibly also including that last interval.

By making corrections for travelling movements, the detection of oestrus becomes more reliable. Travelling movements are defined as movements in which the animal moves from one position to another position for a specific non-oestrus related reason, such as changing paddock, in particular travelling to and from an animal related machine, such as a milking machine, a feeding machine, or a person such as farmer, a veterinarian, or participating in herd movements and running away from a disturbing circumstance, such as a passing train. Herd movements may be travelling movements of at least a substantial part of the herd to a new location (e.g. for herd treatments like preventive claw trimming or flame clipping) or pasture or from pasture to stall/cow house and vice versa, and may also include herd movements wherein a herd starts moving at the same time (in a structured or unstructured way) as the herd is disturbed by an event, such as a passing train or a dog running through the herd. The term unstructured is used here to indicate that different animals of the herd move in different directions at the same time. All these travelling movements may also be referred to as functional activity, i.e. activity that is exhibited for a functional reason (such as milking, feeding, fleeing) and which is thus not related to oestrus.

As a result, on the one hand, the number of false positives is reduced. As non oestrus related activities are corrected for when determining the current activity level, such activities will not trigger a false oestrus attention signal.

Under c) the current activity level is compared to a corresponding baseline activity level. The baseline activity level to which the current activity level is compared to may correspond to the animal or the herd of which the animal is a member. The baseline activity level may also correspond to the time of the day to which the current activity level relates to take into account fluctuations in activity levels that relate to daily patterns, such as night and day patterns or standard milking times, standard feeding times. So, the term corresponding may indicate that the baseline activity level to which the current activity level is compared relates to the same animal and/or time of the day.

According to an embodiment there is provided a method wherein correcting of the current activity level for detected travelling movements is done by discarding (a part of the) activity data related to travelling movements or subtracting activity data related to travelling movements from the activity data. Alternatively, filtering techniques may be employed to correct.

The term discarding is used here to indicate that activity data is not taken into account. In other words, in the case wherein activity data is collected as a set of numbers for consecutive intervals, the number for one or more of such intervals is discarded altogether, as a "too noisy" number so to speak. The discarded data may be deleted, but may also be stored and used for other purposes.

The part of the activity data to be subtracted from the collected activity data may be measured or may be a predetermined value, in each case depending on the travelling movements. This is to be distinguished from subtracting a number not relating to such travelling movements, such as a totally fixed number, an average number for the animal or herd, and so on. This situation is not included in the subtraction.

So, in case a pedometer is used, the number of steps may be counted as an indication of the activity during a certain time interval (e.g. 1000 steps in 2 hours). If it is detected that the animal visited a milking machine during this time interval, the steps counted just before and after the visit to the milking machine (e.g. 15 minutes before and 15 after the visit) may be discarded or subtracted from the total amount of steps counted in the time interval. According to an alternative, a fixed predetermined number of steps (e.g. 250 steps) may be subtracted, for instance based on a known distance between the pasture and the milking machine, but only for a registered milk visit during that interval.

According to an embodiment there is provided a method wherein action b) further comprises b3) determining a baseline activity level based on the activity data.

By determining the base activity level on the activity data measured it is ensured that a baseline activity level is determined which is relevant for the particular animal or herd.

A baseline activity level may be determined for each animal, based on the activity data measured for that animal. The baseline activity level may also be determined for a herd, based on activity data relating to the herd or a predetermined number of animals from the herd or a predetermined portion of the herd.

Typically, the baseline activity level is determined based on activity data from a first time interval and the current activity level is determined based on activity data from a second time interval, the first time interval being at least as long as the second time interval and the second time interval being more recent than the first time interval, such as starting later or in particular being wholly more recent than the first time interval.

The first time interval may be a time interval in the past, for instance a time interval from days or weeks ago from which it is certain that it was a non oestrus time interval, but may also be a recent time interval, such as the last 2 days.

The first time interval may also be formed by a plurality of sub-intervals, such as a plurality of sub-intervals from corresponding time slots from different days (e.g. from 6 am-12 am during the last 10 days).

The second time interval is preferably a recent time interval, such as the current or last interval, of e.g. two hours.

The first time interval is typically in the order of 1 or 2 days or longer. The second time interval is typically 1 or 2 hours. Both the baseline activity level and the current activity level may be computed as a running (weighted) average per time unit or as an absolute value per time unit (e.g. 1000 steps per 2 hours). The current activity level may be computed for each consecutive interval, or for every second time interval, so for instance every 1 or 2 hours, based on activity data relating to that particular time interval, or for any other desired set of intervals.

The method, or at least action c), may be performed each time a new current activity level is available. Actions a), b) and c) may be performed every second time interval, for instance every 2 hours. Alternatively, one or more of the actions a), b) and c) may be performed continuously, while b) and c) are performed every second time interval.

According to an embodiment there is provided a method wherein action b) further comprises
b4) correcting the baseline activity level for detected travelling movements.

As the baseline activity level will typically be lower when activity is corrected for travelling movements when determining a baseline activity level, detecting oestrus related activity can be done in a more reliable way as the noise to signal ratio is improved. This way, the number of false negatives is reduced as well as oestrus related activity can be better distinguished from the baseline.

According to an embodiment there is provided a method wherein action c) comprises generating an oestrus attention signal if more than a predetermined number of consecutive current activity levels exceed the corresponding baseline activity levels with more than a predetermined amount or percentage. Herein, "consecutive current levels" means "levels as consecutively determined", such as for consecutive intervals, or during a certain time when the current level is determined continuously.

For instance, in case a new current activity level is determined every second time interval, e.g. every 2 hours, an oestrus attention signal may be generated when the current activity level exceeded the corresponding baseline activity levels with more than a predetermined amount or percentage three or more times in a row, indicating that the animal has exhibited an increased oestrus-related activity for more than 6 hours. The predetermined number may vary and may for instance depend on the type of animal or the length of the second time interval. The predetermined number may be 1, 2, 3, 4 or any other suitable integer number.

According to an embodiment there is provided a method wherein detecting travelling movements of the animal comprises detecting at least one of:
a milking machine visit,
a feeding machine visit,
a drinking station visit,
a herd movement,
an animal travelling movement.

Detection of one or more of the above events is an indication that the animal exhibits activity which is not related to oestrus. Especially in free grazing systems in combination with milking machines and possibly feeding machines, the animal needs to travel a relatively large distance to visit the milking or feeding machine. Such activity is not related to oestrus and correcting the activity data for such travelling movements increases the reliability of detecting oestrus. Other travelling movements, such as other purposive movements, are not excluded. Herein, "purposive" means that the animal has an obvious purpose in travelling from A to B, and non-oestrus animals would have the same purpose. Based on experience, the skilled farmer will be able to think of such travelling movements. According to an embodiment, detecting travelling movements of the animal is done using only activity data of the animal, i.e. not taking into account activity data of other animals. According to an embodiment there is provided a method wherein detecting travelling movements comprises receiving a milking machine visit notification relating to the animal from a milking machine, possibly indicating a milking machine visiting time.

The milking machine may be a milking robot.

The milking machine may comprise an animal identification device to identify which animal visits the milking machine and may possibly comprise a clock to determine the milking machine visiting time. The animal identification device may be provided at an entrance of the milking machine, but may also be positioned inside the milking machine.

The milking machine visiting time may be the time the animal reports to the milking machine, the time the animal is milked (start and/or end), or the time the animal leaves the milking machine. It will be understood that the milking machine visiting notification may also be triggered when the animal visits the milking machine without being milked.

When the animal reports to an animal identification device at the milking machine, activity data in relation to this can be corrected for when determining at least one of the current activity level and the baseline activity level.

For instance, activity data from a time interval (e.g. 15 minutes) before the time on which the animal was identified by the milking machine can be discarded as during this time interval the animal travelled to the milking machine. This activity is not related to oestrus. Also, activity data from a time interval (e.g. 15 minutes) after the time on which the animal was identified or left the milking machine can be discarded as during this time interval the animal will exhibit a typical behaviour, such as travelling back to the herd or pasture. The activity data relating to the actual milking may also be discarded.

Alternatively, the activity data is corrected with a predetermined amount, such as a predetermined amount of steps in case the activity is measured using a pedometer. The predetermined amount may be set by an operator and may for instance depend on a known distance between the milking machine and the pasture. The predetermined amount also includes a predetermined percentage of the measured activity data (e.g. 10%). An advantage of correcting the activity data by subtracting such a value of e.g. the average number of steps is that the data itself could still indicate oestrus if the animal rambles hither and thither instead of travels to the milking machine, as the number of steps required would be (much) increased over a direct route, which the animals usually take.

This embodiment is in particular advantageous when milking machines are used in free grazing systems which can be visited by the animal at any time and where the animal is forced to travel a relatively large distance to visit the milking machine.

According to an embodiment there is provided a method wherein detecting travelling movements comprises receiving a feeding machine visit notification relating to the animal from a feeding machine, possibly indicating a feeding machine visiting time.

The feeding machine may comprise an animal identification device to identify which animal visits the feeding machine and may comprise a clock to determine the feeding machine visiting time. The feeding machine visiting time may be the time the animal reports to the feeding machine, the time the animal feeds (start and/or end), or the time the animal leaves the feeding machine. It will be understood that the feeding machine visiting notification may also be triggered when the animal visits the feeding machine without being fed.

When the animal reports to an animal identification device at the feeding machine, activity data in relation to this can be discarded. For instance, activity data from a time interval before the time on which the animal was identified can be discarded as during this time interval the animal travelled to the feeding machine. Also, activity data from a time interval after the time on which the animal was identified or left the feeding machine can be discarded as during this time interval the animal will exhibit a typical behaviour, such as travelling back to the herd or pasture. The activity data relating to the actual feeding may also be discarded, especially when the activity data is collected using a neck collar.

Alternatively, the activity data is corrected with a predetermined amount, such as a predetermined amount of steps in case the activity is measured using a pedometer or a predetermined amount of neck movements when activity is measured using a neck collar.

According to an alternative, the above embodiment may relate to a drinking station instead of a feeding machine.

According to an embodiment there is provided a method wherein detecting travelling movements comprises collecting activity data from a plurality of animals being members of a herd of which the animal is a member, and detecting herd movement by analyzing the activity data from the plurality of animals.

Herd activity can be identified by analyzing the activity data of a plurality of animals from the same herd. For instance, when more than a predetermined number of animals or a predetermined percentage of animals with respect to the total herd show increased activity data, herd activity can be identified. Increased activity data may for instance be determined by comparing the current activity data of the plurality of animals with a baseline activity level of the respective individual animals or of the herd.

An animal participating in herd activity exhibits activity that is not oestrus related. For instance, when a herd moves from one location to an other, to a specific location to receive herd treatment (e.g. claw trimming or flame clipping) or is disturbed by an event, such as a passing train, the animal will exhibit non oestrus related activity.

According to an embodiment there is provided a method wherein detecting travelling movements comprises receiving and analyzing positioning data relating to the animal and/or relating to a plurality of animals being members of a herd of which the animal is a member.

The positioning data may be measured by an animal locator, which may be embodied in any suitable way. The animal locator may for instance be embodied by a positioning device attached to the animal. Such a positioning device may be a GNSS-based device (global navigation satellite system) or a land-based positioning system.

The animal locator may also be embodied by e.g. a camera system provided with pattern recognition software which is able to recognize animals and determine their position, a stable based systems with tracking devices such as RF-ID chip tracking and so on.

Travelling movement of the animal can be identified by analyzing the received positioning data relating to the animal. From the positioning data it can be analyzed if the animal travelled from a first location to a second location, e.g. from a grazing position to the milking machine, which is non oestrus related activity. Detecting travelling movement may be done by analyzing the positioning data and determining if the animal moved more than a predetermined distance (for instance 300 meters) within a predetermined time interval (such as 5 minutes). If so, the activity data relating to this movement may be discarded.

Travelling movement of the animal can also be identified by analyzing the received positioning data relating to the plurality of animals being members of the herd of which the animal is a member. If the positioning data of a predetermined number of animals or a predetermined percentage of animals with respect to the total herd show a simultaneous travelling movement, herd movement can be detected.

According to an embodiment there is provided a method wherein detecting travelling movements comprises collecting data from one or more animal identification devices.

The one or more animal identification devices are arranged to identify an animal passing by using any suitable way of identification.

By collecting data from one or more animal identification devices knowledge can be obtained about travelling movements of the animal. For instance, if the animal is identified by two animal identification devices at different locations, it can be concluded that the animal at least performed a travelling movement to cover the distance between the two animal identification devices. Such movement can be regarded as a travelling movement which is non oestrus related.

Travelling movements may also be detected based on a single animal identification device. For instance, if an animal is identified by an animal identification device position on a path or route from cow house to pasture, it can be concluded that the animal at least performed a travelling movement to cover the distance between the cow house and the pasture.

According to an embodiment there is provided a method wherein action c) comprises detecting if the current activity level exceeds the corresponding baseline activity level with more than a predetermined amount or percentage, wherein the predetermined amount or percentage is related to a variance of the activity data, in particular the variance in the activity data used to determine the baseline activity level.

The variance may for instance be the standard deviation or a multiple (e.g. 2 or 2.5) thereof. By using the variance of the activity data of the animal as a measure for the predetermined amount, the test under c) is made animal-dependent.

According to an aspect there is provided a system for generating an oestrus attention signal for one or more cattle animals, the system comprising one or more activity measurement devices for collecting activity data of the one or more animals and a processing device, wherein the one or more activity measurement devices are arranged to transmit activity data to the processing device, the processing device being arranged to
  a) receive activity data from the one or more activity measurement devices, b) compute current activity levels based on the activity data for the one or more animals,
  c) decide whether to generate an oestrus attention signal for an animal by comparing the at least one current activity level for the respective animal to a corresponding baseline activity level, characterized in that the processing device is arranged to
  b1) detect travelling movements of the animal and
  b2) correct the current activity level for detected travelling movements.

Herein, the detection of travelling movements is in accordance with any or all of the possibilities mentioned for the method described hereinbefore. Note that it is possible for the system to comprise a separate device for detecting the travelling movements. Such a separate device could for example comprise an animal locator system, as described above, while activity data are collected by means of one or more pedometers or other activity measurement devices. In such cases, the processing device may correct the activity data, compute activity levels and so on, based on both the activity data as collected by the activity measurement devices, and on the travelling movement as detected by the separate device such as the animal locator system.

The processing device may be computer device, for instance a computer dedicated to generating an oestrus attention signal, including a mobile telephone, tablet, laptop and desktop. The processing device may comprise input means, output means, a processor and a memory accessible by the processor. The memory may comprise instruction lines readable and executable by the processor. The processing device may also be formed by a plurality of cooperating devices and may also (partially) take place in a network of interconnected devices (including cloud computing).

The input means may be formed by wired and/or wireless input means which enable the processing device to communicate with the activity measurement devices, such as a pedometer attached to the animal, or to a remote computer comprising activity data. The received activity data may be stored in the memory. Receiving and storing may be controlled by the processor.

The processor may be formed by a central processing unit which is arranged to read and write data from and to the memory.

The output means may be formed by hardware means, like a display or the like. The output means may also be formed by a wired or wireless output such that the oestrus attention signal can be outputted to a remote device, such as a remote computer, for instance being a mobile telephone of a farmer.

According to an embodiment the processing device is arranged to correct the current activity level with respect to an animal for detected travelling movements of the animal by discarding activity data related to travelling movements or subtracting activity data related to travelling movements from the activity data.

According to an embodiment the processing device is arranged to b3) determine a baseline activity level based on the activity data.

The baseline activity level may be determined for each animal individually based on activity data corresponding to that particular animal, or may be determined for a herd based on activity data corresponding to at least a number of animals member of the herd.

According to an embodiment the processing device is arranged to b4) correct the baseline activity level for detected travelling movements.

According to an embodiment the processing device is arranged to generate an oestrus attention signal with respect to an animal if more than a predetermined number of consecutive current activity levels of that animal exceed the corresponding baseline activity levels with more than a predetermined amount or percentage.

According to an embodiment the processing device is arranged to detect in relation to the animal at least one of:
  a milking machine visit, a feeding machine visit,
a drinking station visit,
a herd movement,
an animal travelling movement.

Information regarding one of the above events may be received by the processing device via input means. Also, the processor may be arranged to detect one or more of the above events based on activity data received (via the input means) relating to the animal and/or a group of animals.

According to an embodiment the processing device is arranged to detect travelling movements by receiving milking machine visit notifications relating to animals, possibly indicating a milking machine visiting time.

According to an embodiment the processing device is arranged to detect travelling movements by receiving feeding machine visit notifications relating to animals, possibly indicating a feeding machine visiting time. The feeding machine may be a drinking machine.

According to an embodiment the processing device is arranged to detect travelling movements by receiving activity data from a plurality of animals being members of a herd, and detecting herd movement by analyzing the activity data from the group of animals.

According to an embodiment the processing device is arranged to detect travelling movements by receiving and analyzing positioning data relating to the animal and/or relating to a plurality of animals being members of a herd of which the animal is a member.

According to an embodiment the processing device is arranged to detect travelling movements by collecting data from one or more animal identification devices.

According to an embodiment the processing device is arranged to perform action c) by detecting if the current activity level of an animal exceeds the corresponding baseline activity level with more than a predetermined amount or percentage, wherein the predetermined amount or percentage is related to a variance of the activity data, in particular the variance in the activity data used to determine the baseline activity level of that animal.

According to an aspect there is provided a computer program product comprising instructions which can be loaded by a computer device and when loaded enable the computer device to perform any one of the methods described above. The computer device may be the processing device mentioned above.

According to an aspect there is provided a computer readable medium comprising a computer program product according to the above.

According to an aspect there is provided a computer device arranged to perform the any one of the methods described above.

SHORT DESCRIPTION OF THE DRAWINGS

Figure 2:
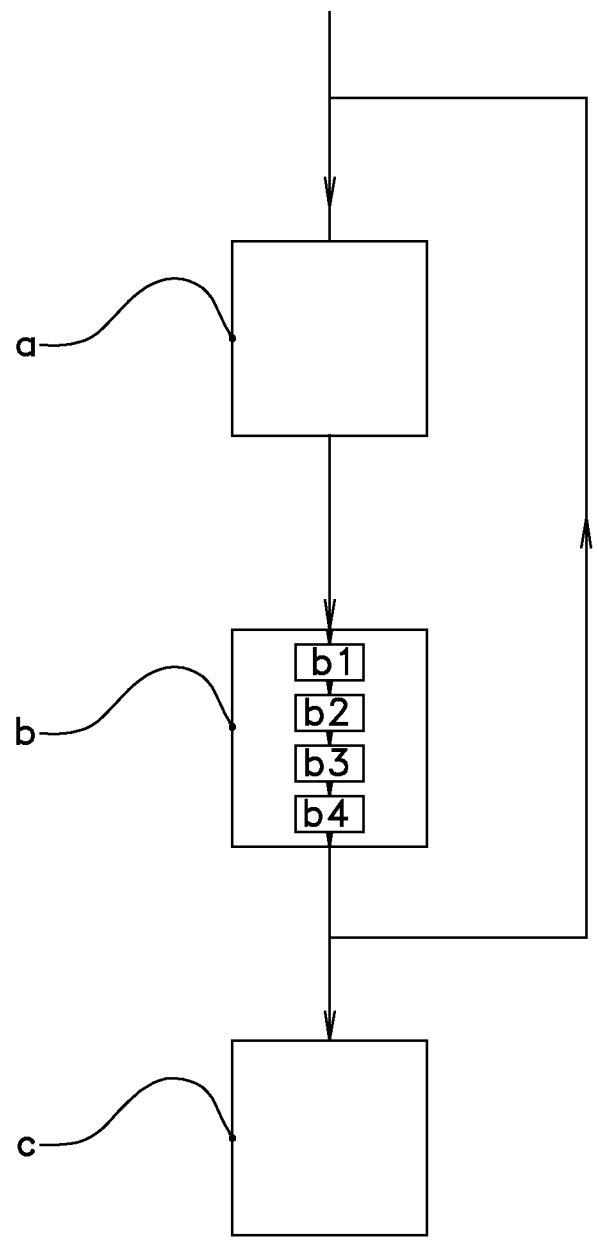

Embodiments will now be described, by way of example only, with reference to the accompanying schematic drawings in which corresponding reference symbols indicate corresponding parts, and in which:
FIG. 1 schematically depicts a plan of a free grazing system according to an embodiment,
FIG. 2 schematically depicts a method according to an embodiment.

DETAILED DESCRIPTION

FIG. 1 shows a schematic plan of a free grazing system comprising a cow house 10, a milking machine 11, a feeding machine 12, two separated pastures 13, 14 and a herd comprising a plurality of animals C, e.g. cows. Inside the cow house 10 are cubicles 15 for the animals. One of the pastures 13 comprises a drinking station 18, the other pasture 14 comprises a stand-alone data station 19. In between the cow house 10 and the pastures 13, 14 is a travelling path 16.

The cow house 10 comprises an exit 21 with a one way gate 20 and an entrance 22 with a one way gate 20.

The animals C are equipped with activity measurement devices A for collecting activity data of the animals C. The activity measurement devices A for collecting activity data may be pedometers attached to a leg of the animal C or a collar as shown in FIG. 1.

The animals C are also equipped with an identification tag, such as a leg or neck responder. In the embodiment shown in FIG. 1, the identification tag is integrated with the activity measurement devices A.

The free grazing system may comprise one or more animal identification devices 17 to identify animals by means of the identification tag and possible collect data from the activity measurement device A. According to the embodiment shown in FIG. 1, animal identification devices 17 are provided at the milking machine 11, the feeding machine 12, the exit 21, the entrance 22, the drinking station 18 and the stand-alone data station 19.

Although not shown, animal identification devices 17 may also be provided half way travelling path 16 or at the entrance of the pastures 13, 14.

An animal identification device 17 may be provided at the milking machine 11 to decide if an animal may be milked and register the milking details of the animal C. An animal identification device 17 may be provided at the feeding machine 12 to decide if an animal C may be fed, and if so to determine the ration. An animal identification device 17 may be provided at the exit 21 to determine if an animal may exit the cow house 10. An animal identification device 17 may be provided at the entrance 22 to register animals C entering the cow house 10. An animal identification device 17 may be provided at the drinking station 18 to monitor drinking behaviour and the stand-alone data station 19 may be provided to collect activity data from the activity measurement devices A. In fact, all identification devices 17 may be used to collect activity data from the activity measurement devices A. The activity measurement devices A may comprise a memory to store activity data which may be read by the activity measurements devices A and forwarded to a processing device 100, which will be discussed in more detail below.

In a free grazing system with a voluntary milking system the animals C are allowed to travel freely at least during a certain time of the day between and through the pastures 13,14 and the milking machine 11. Typically for free grazing systems the animals C need to cover a substantial distance to travel from the pasture to the milking machine 11, typically more than 100 meters.

The activity data collected by the activity measurement devices A may be transmitted to a processing device 100 for generating an oestrus attention signal for an animal C at regular time intervals. The activity data may be transmitted directly from the activity measurement devices A to the processing device 100 and/or may be collected by the animal identification devices 17 when an animal is identified and forwarded from the animal identification devices 17 to the processing device 100.

The processing device 100 for generating an oestrus attention signal is a computer device comprising input means 101, processor 102 and output means 103. The input means 101 may be arranged to receive data from a remote computer or device, such as animal identification devices 17 or activity measurement devices A. The output means 103 may be arranged to output data or signals, such as an attention signal. Input and output may be wireless, wired or a combination thereof. The input means 101 and the output means 103 may be integrated into combined input-output means.

The processor 102, for instance a CPU, is arranged to communicate with the input and output means 101, 103. The processing device 100 further comprises a memory 104. The memory 104 may comprise instructions lines readable and executable by the processor 102 to provide the processing device 100 with the functionality according to the embodiments. The processor 102 may further access the memory 104 to store and read data, such as activity data, a current activity level, a baseline activity level.

The processing device 100 is arranged to collect activity data via the input means 101 from the activity measurement devices A and/or via the identification devices 17. The processing device 100 is further arranged to generate an oestrus attention signal via the output means 103, for instance by sending an attention signal to a remote computer or mobile telephone or to a display and/or speaker.

The processing device 100 is arranged to perform the following method:
a) collecting activity data of at least one animal C,
b) computing a current activity level based on the collected activity data,
c) deciding whether to generate an oestrus attention signal by comparing at least one current activity level to a corresponding baseline activity level.

This method is schematically depicted in FIG. 2, showing that action a) comprises input from at least one activity measurement devices A, action c) results in a generated oestrus attention signal or not and actions a) and b) are looped and performed at regular time intervals, e.g. of 2 hours.

The current activity level may be expressed as a number of steps per time unit, such as 1000 steps in the previous 2 hours.

As cows C typically exhibit an increased activity in association with oestrus the method comprises determining a current activity level and comparing it to a reference value, referred to as a baseline activity level. Especially in free grazing systems, the animals C exhibit a large amount of travelling movements, which are not related to oestrus, such as:
 a milking machine visit,
 a feeding machine visit,
 a drinking station visit,
 a herd movement,
 an animal travelling movement.

An animal travelling movement may comprise travelling movements to a milking machine 11, a feeding machine 12, a drinking station 18, a travelling movement from the cow house 10 to one of the pastures 13 and vice versa, travelling movement from one pasture 13 to an other pasture 14, travelling movement from one position inside a pasture 13 to another position inside the same pasture 13.

The processing device 100 is therefore arranged to detect such travelling movements of the animal C and correct for these travelling movements when deciding to generate an oestrus attention signal or not in relation to a particular animal C.

An animal C may be present in the pasture 13. This may be detected as the animal C left the cow house 10 via exit 21 where it was identified by the identification device 17 or was identified by one of the identification devices 17 in the pastures 13, 14.

Activity data are constantly measured by the activity measurement device A connected to the animal C and these data are sent to the processing device 100 at regular time intervals to determine a current activity level for this animal C and possibly to determine a baseline activity level for this animal C. The current activity level may be determined at regular time intervals, for instance every two hours.

At a certain moment in time, the animal C is identified by the identification device 17 present in the milking machine 11. A milking machine visit notification is sent to the processing device 100 relating to this animal C, possibly indicating a milking machine visiting time.

This provides evidence that the animal C exhibited a travelling movement from the pasture 13 to the milking machine 11. As the distance between the pasture 13 and the milking machine 11 is known, the processing device 100 corrects the current activity level of the current time interval in which the animal C visited the milking machine 11 by subtracting a predetermined amount of activity or discarding activity data related to the milking visit.

For instance, in case 1000 steps are recorded by the activity measurement device A in between 14h00 and 16h00 and a milking machine visit notification is received at 15h00, the 1000 steps may be corrected to 750 steps to take into account the travelling movement between the pasture 13 and milking machine 11.

Alternatively, instead of correcting the amount of steps with a predetermined amount of steps, the correction may be done by discarding all activity data measured in a predetermined time interval in relation to the milking machine visit, for instance by discarding all activity data measured between 14h45 and 15h15.

This last example may also be used in case the animal C was already present in the cow house 10 before visiting the milking machine 11 to take into account an specific activity pattern which animals C may exhibit before and after milking.

The above example of a milking machine visit may mutatis mutandis be applied to correct for a visit to feeding machine 12.

According to a further example, the processing device 100 may detect travelling movements by collecting and analyzing data received from one or more animal identification devices 17 positioned at known locations, the data comprising identification data of animals C identified by the animal identification devices 17. For instance, in case an animal C is identified by an animal identification device 17 positioned in the cow house 10 (e.g. milking machine 11, feeding machine 12, exit 22) and at a later moment in time by an animal identification device 17 in the pasture 13, 14 (e.g. drinking station 18, stand-alone data station 19), the processing device 100 may subtract or discard activity data to take into account the activity associated with the travelling movement from the cow house 10 to the pasture 13, 14.

The processing device 100 may further detect travelling movements by collecting and analyzing activity data from a plurality of animals C part of the herd. The activity data from the plurality of animals C provides information about herd movements if all members of the herd or at least a predetermined number or percentage of the herd exhibits increased activity at the same time. This is an indication for a herd movement, i.e. from one pasture 13 to another pasture 14 or unstructured herd movements for instance caused by an unexpected event as a passing train, landing balloon or a dog entering the pasture.

The processing device 100 may further detect travelling movements by receiving and analyzing positioning data relating to the animal and/or relating to a plurality of animals being members of a herd of which the animal is a member.

In an embodiment, the activity measurement devices A comprise animal locators. The animals C may for instance be equipped with an animal locator embodied by a positioning device, such as a GNSS-based device. Alternative animal locators may be conceived which provide positional data of the animals C. By measuring, collecting and analyzing positional data, the processing device 100 may detect travelling movements. Travelling movements may be detected by analyzing if the animal C travelled more than a predetermined distance in a predetermined amount of time.

The animal locators may also be formed by a camera system provided with pattern recognition software to determine the position and travelling movements of the animals C.

From the above it is clear that activity data relating to travelling movements may be corrected for when determining a current activity level. The travelling movements may also be used to correct the baseline activity, which may also be based on the measured activity level. This will typically result in a lower baseline activity level, or at least a level that is more free from "noise" as generated by deliberate and purposive movements that could blur oestrus generated activity, and thus a more sensitive detection method.

So, with reference to FIG. 2, the method for monitoring oestrus of a cattle animal C comprises
 a) collecting activity data of the animal (C),
 b) computing a current activity level based on the activity data,
 b1) detecting travelling movements of the animal (C) and
 b2) correcting the baseline activity level for detected travelling movements.
 c) deciding whether to generate an oestrus attention signal by comparing at least one current activity level to a corresponding baseline activity level.

Action b) may further optionally comprise action b3) in which the baseline activity level is computed based on the activity data collected in action a). Also, optionally action b) may comprise correcting the baseline activity level for detected travelling movements.

The method generates and the processing device 100 is arranged to generate an oestrus attention signal or not by comparing at least one current activity level to a corresponding baseline activity level. An oestrus attention signal may be generated in case more than a predetermined number of consecutive current activity levels exceed the corresponding baseline activity levels with more than a predetermined amount or percentage.

Further Embodiments

According to a further embodiment there is provided a method for monitoring oestrus of a cattle animal, in particular a cow (C), the method comprising:
 a) collecting activity data of the animal (C),
 b) computing a current activity level based on the activity data, and
 c) deciding whether to generate an oestrus attention signal by comparing at least one current activity level to a corresponding baseline activity level,
 characterized in that action b) further comprises
  b1) detecting travelling movements of the animal (C),
  b2') determining a baseline activity level based on the activity data, and
  b3') correcting the baseline activity level for detected travelling movements.

Further provided is a system for generating an oestrus attention signal for one or more cattle animals (C), comprising one or more activity measurement devices (A) for collecting activity data of the one or more animals (C) and a processing device (100), wherein the one or more activity measurement devices (A) are arranged to transmit activity data to the processing device (100), the processing device (100) being arranged to
 a) receive activity data from the one or more activity measurement devices (A),
 b) compute current activity levels based on the activity data for the one or more animals (C),
 c) decide whether to generate an oestrus attention signal for an animal by comparing the at least one current activity level for the respective animal (C) to a corresponding baseline activity level,
 characterized in that the processing device (100) is arranged to
  b1) detect travelling movements of the animal (C),
  b2') determine a baseline activity level based on the activity data, and
  b3') correct the baseline activity level for detected travelling movements.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A system for generating an oestrus attention signal for one or more cattle animals, the system comprising:
 a milking robot that identifies which animal of the one or more animals visits the milking robot;
 a clock to determine a milking robot visiting time of the animal to the milking robot;
 an activity measurement sensor configured to collect activity data of the animal; and
 a processing device;
 wherein the activity measurement sensor is configured to transmit activity data to the processing device, the processing device being configured to:
  a) receive the activity data from the activity measurement sensor,
  b) compute current activity levels based on the activity data for the animal, and
  c) decide whether to generate an oestrus attention signal for the animal by comparing at least one current activity level for the animal to a corresponding baseline activity level,
 wherein the processing device is further configured to receive the activity data from the activity measurement sensor by being configured to detect travelling movements of the animal by receiving a milking robot visit notification relating to the animal and/or indicating the milking robot visiting time,
 the activity data includes steps, head/neck movements, or walking of the animal,
 the travelling movements are movements in which the animal moves to and from the milking robot,
 wherein the processing device is further configured to compute current activity levels based on the activity data for the animal by being configured to correct the current activity level for detected travelling movements, wherein the processing device is further configured to correct the current activity level with respect to the animal for detected travelling movements of the animal by discarding activity data related to the travelling movements, associated with the milking robot visit notification and/or the milking robot visiting time, or subtracting activity data related to the travelling movements, associated with the milking robot visit notification and/or the milking robot visiting time, from the activity data, and wherein the processing device is further configured to generate, based on the decision, the oestrus attention signal with respect to the animal if more than a predetermined number of consecutive current activity levels of the animal exceed the corresponding baseline activity levels with more than a predetermined amount or percentage.

2. A system according to claim 1, wherein the processing device is configured to:

b3) determine a baseline activity level based on the activity data.

3. A system according to claim 2, wherein the processing device is configured to:

b4) correct the baseline activity level for detected travelling movements.

4. A system according to claim 1, wherein the processing device is configured to detect a milking robot visit.

5. A system according to claim 1, wherein the processing device is configured to detect travelling movements by collecting data from the milking robot.

6. A system according to claim 1, wherein the processing device is configured to perform c) by detecting if the current activity level of the animal exceeds the corresponding baseline activity level with more than the predetermined amount or percentage, wherein the predetermined amount or percentage is related to a variance of the activity data, in particular the variance in the activity data used to determine the baseline activity level of the animal.

* * * * *